US012678443B2

(12) United States Patent
Oki et al.

(10) Patent No.: US 12,678,443 B2

(45) **Date of Patent: *Jul. 14, 2026**

(54) MEDICAMENT FOR PREVENTING AND/OR TREATING DRY EYE

(71) Applicants: Santen Pharmaceutical Co., Ltd., Osaka (JP); Boehringer Ingelheim International GMBH, Ingelheim am Rhein (DE)

(72) Inventors: Kenji Oki, Minoh (JP); Takashi Nagano, Osaka (JP); Nagayoshi Asano, Ikoma (JP); Koushi Fujisawa, Ikoma (JP)

(73) Assignees: SANTEN PHARMACEUTICAL CO., LTD., Osaka (JP); BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 80 days.

This patent is subject to a terminal disclaimer.

(21) Appl. No.: 18/655,985

(22) Filed: May 6, 2024

(65) Prior Publication Data

US 2024/0293417 A1 Sep. 5, 2024

Related U.S. Application Data

(63) Continuation of application No. 17/722,947, filed on Apr. 18, 2022, now Pat. No. 12,005,063, which is a continuation of application No. 17/513,593, filed on Oct. 28, 2021, now Pat. No. 11,331,322.

(30) Foreign Application Priority Data

Sep. 15, 2021 (JP) ................................ 2021-150112

(51) Int. Cl.

| | |
|---|---|
| ***C07D 265/36*** | (2006.01) |
| ***A61K 31/536*** | (2006.01) |
| ***A61K 31/538*** | (2006.01) |
| ***A61P 27/04*** | (2006.01) |

(52) U.S. Cl.

CPC .......... *A61K 31/536* (2013.01); *A61K 31/538* (2013.01); *A61P 27/04* (2018.01)

(58) Field of Classification Search

CPC ...... C07D 265/36; A61K 31/536; A61P 27/04

See application file for complete search history.

(56) References Cited

U.S. PATENT DOCUMENTS

| | | | |
|---|---|---|---|
| 5,981,607 | A | 11/1999 | Ding et al. |
| 11,331,322 | B1 | 5/2022 | Oki et al. |
| 12,005,063 | B2 | 6/2024 | Oki et al. |
| 2003/0008805 | A1 | 1/2003 | Honma et al. |
| 2022/0098164 | A1 | 3/2022 | Collingwood et al. |
| 2023/0087826 | A1 | 3/2023 | Oki et al. |
| 2024/0374607 | A1 | 11/2024 | Oki et al. |

FOREIGN PATENT DOCUMENTS

| | | | |
|---|---|---|---|
| CN | 110062625 | A | 7/2019 |
| WO | WO 2001/041806 | A1 | 6/2001 |
| WO | WO 2011/068786 | A2 | 6/2011 |
| WO | WO 2017/043612 | A1 | 3/2017 |
| WO | WO 2018/108669 | A1 | 6/2018 |
| WO | WO 2019/020634 | A2 | 1/2019 |
| WO | WO 2019/230230 | A1 | 12/2019 |
| WO | 2020249956 | A1 | 12/2020 |
| WO | WO 2020/251926 | A1 | 12/2020 |
| WO | WO 2023/042851 | A1 | 3/2023 |

OTHER PUBLICATIONS

U.S. Appl. No. 18/691,241, filed Mar. 12, 2024, Oki et al.

Notice of Allowance mailed Jan. 20, 2022 in U.S. Appl. No. 17/513,593 (7 pages).

International Search Report and Written Opinion dated Nov. 29, 2022 for PCT/JP2022/034383 (8 pages).

Office Action issued Jul. 27, 2023 in Chinese Patent Application No. 202280006228.4 (19 pages, including English translation) (note: Chinese Patent Application No. 202280006228.4 is a foreign counterpart of U.S. Appl. No. 17/722,947).

Shen, J. et al., 2013, "Olodaterol hydrochloride, a long acting bronchodilator," Shanghai Medical & Pharmaceutical Journal, 34(15):19-21 (9 pages including English translation).

Notice of Allowance mailed Feb. 7, 2024 in U.S. Appl. No. 17/722,947 (5 pages).

Office Action dated Oct. 10, 2023 in U.S. Appl. No. 17/722,947 (5 pages).

International Preliminary Report on Patentability for International Patent Application No. PCT/JP2022/034383, International Bureau of WIPO, Switzerland, issued Mar. 5, 2024 (4 pages).

Extended European Search Report mailed Jul. 22, 2025 for EP 22869998.9 (8 pages).

Masakazu Ichinose et al., 2015, "Efficacy and safety of the long-acting ß2-agonist olodaterol over 4 weeks in Japanese patients with chronic obstructive pulmonary disease," International Journal of COPD, 10:1673-1683.

United States Patent and Trademark Office, Non-Final Office Action for U.S. Appl. No. 18/691,241 dated Mar. 13, 2026.

*Primary Examiner* — Brenda L Coleman

(74) *Attorney, Agent, or Firm* — Jones Day

(57) ABSTRACT

A compound useful for preventing or treating dry eye and a medicament for preventing and/or treating dry eye comprising the same which does not substantially impact on the intraocular pressure are provided. A method of preventing and/or treating dry eye in a subject in need thereof, comprising administering a therapeutically effective amount of olodaterol or a salt thereof to the subject is also provided.

10 Claims, 3 Drawing Sheets

[Fig. 1]
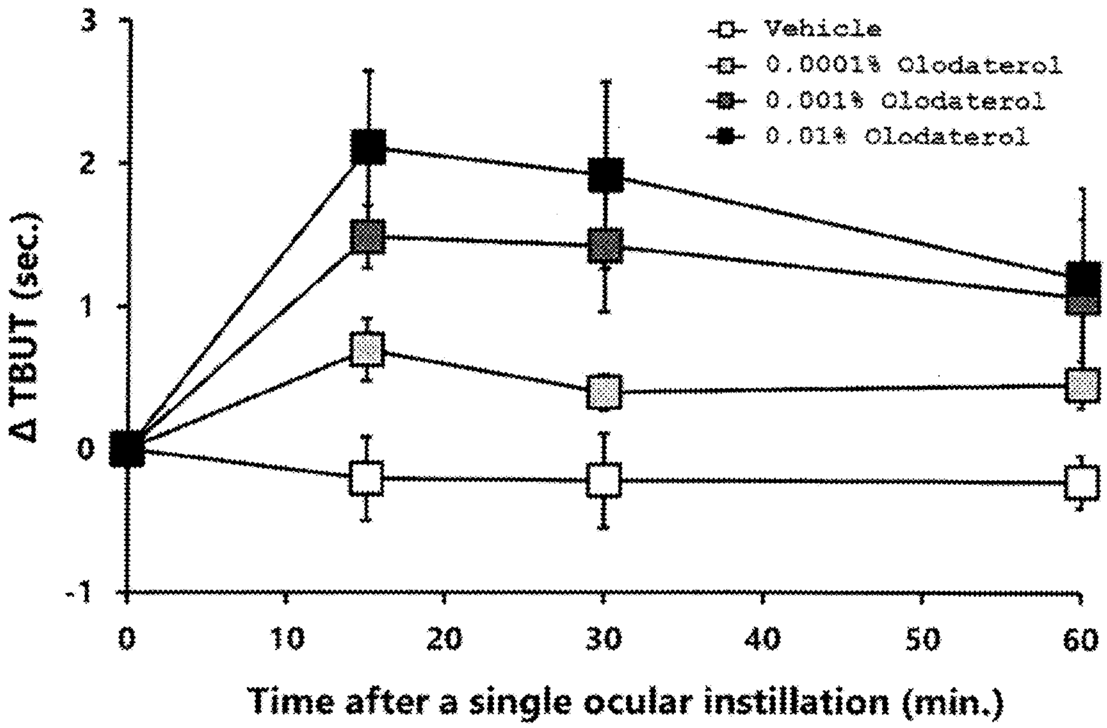
[Fig. 2]
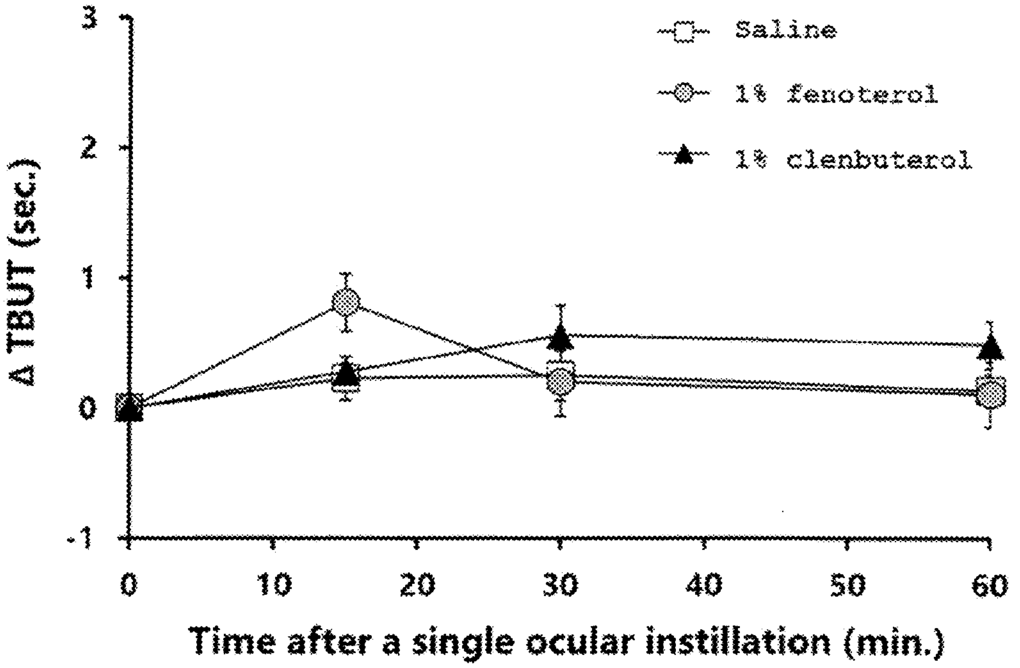

[Fig. 3]
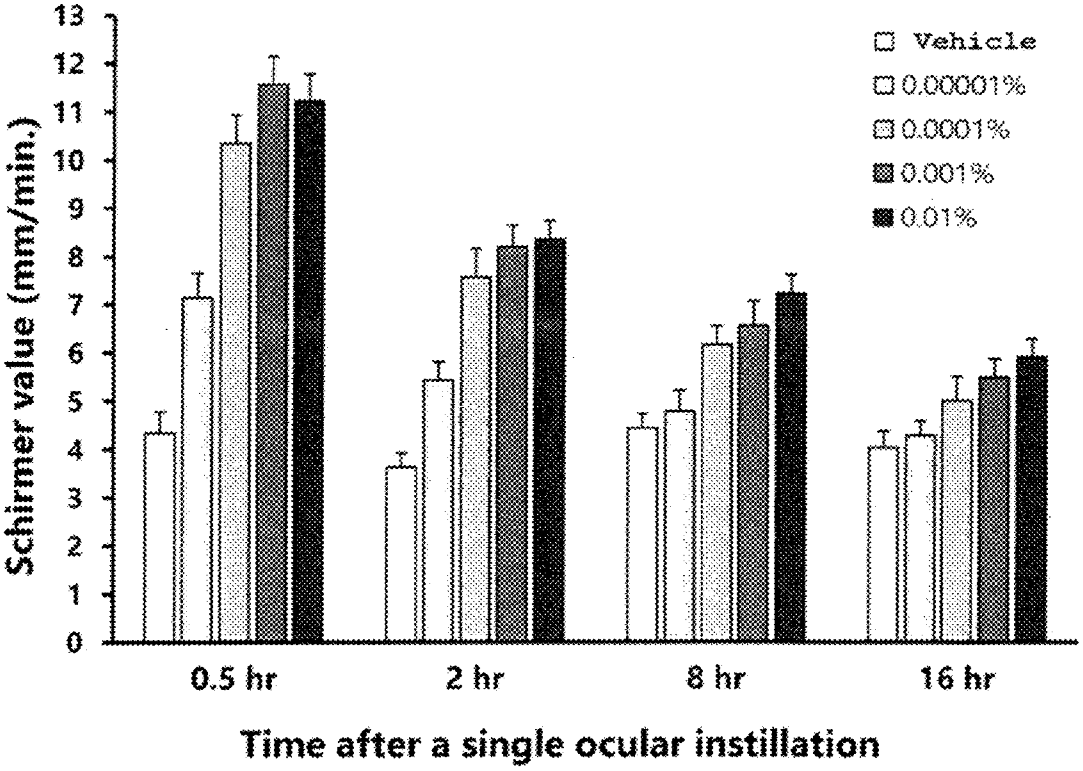

[Fig. 4]
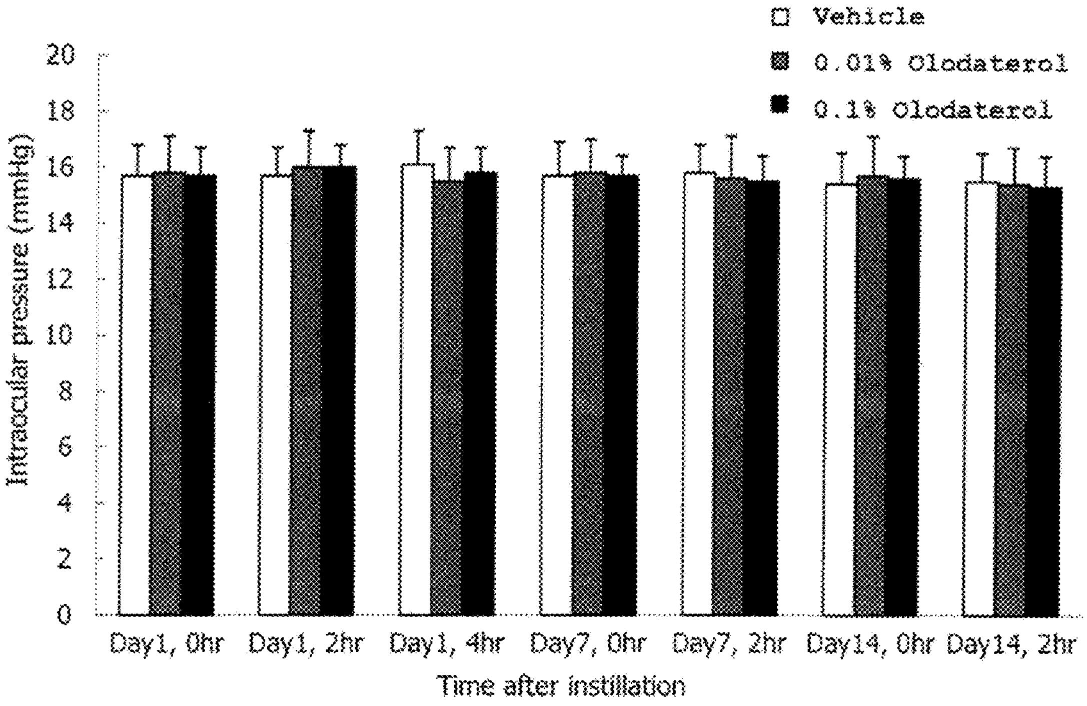

MEDICAMENT FOR PREVENTING AND/OR TREATING DRY EYE

CROSS-REFERENCE TO RELATED APPLICATIONS

The present application is a continuation of U.S. patent application Ser. No. 17/722,947, filed Apr. 18, 2022, currently allowed, which is a continuation of U.S. patent application Ser. No. 17/513,593, filed Oct. 28, 2021, now U.S. Pat. No. 11,331,322, issued May 17, 2022, which claims priority to Japanese patent application serial number 2021-150112, filed on Sep. 15, 2021, the entire contents of each of which are herein incorporated by reference.

TECHNICAL FIELD

The present invention relates to a method of preventing and/or treating dry eye in a subject in need thereof, comprising administering olodaterol or a salt thereof to the subject.

BACKGROUND ART

Dry eye is a disease causing dry-eye symptoms such as discomfort feelings on eyes and abnormalities in visual performance, associated with abnormalities in tear volume or quality, which may cause disorders on the surface of eyes such as cornea. The abnormalities in tear volume mainly refer to the condition of low lacrimal secretion, which is an index of dry eye based on the tear volume. Regarding the abnormalities in tear quality, abnormalities in tear ingredients such as few lipid or protein components contained in tears may deteriorate the stability of tear film, which may then cause dryness on the surface of eyes even with tear secretion.

Clenbuterol and fenoterol are known as a selective $\beta_2$ adrenergic receptor agonist, and have been confirmed to enhance secretion of tears and tear proteins (Patent Literature 1).

Another $\beta_2$ adrenergic receptor agonist, salbutamol, has also been confirmed to enhance lacrimal secretion (Patent Literature 2). Whereas, it has been reported that salbutamol did not have sufficient effects on the treatment of dry eye, and increased intraocular pressure (Patent Literature 3).

Patent Literature 4 lists dry eye as an example of various symptoms associated with autoimmune disease, systemic lupus erythematosus (SLE), and discloses the use of β2 adrenergic receptor agonist in the treatment of SLE. It discloses tests with some drugs in a kidney disease model, but it does not disclose any tests for the treatment of dry eye with β2 adrenergic receptor agonists.

Olodaterol (chemical name: 6-hydroxy-8-((1R)-1-hydroxy-2-{[2-(4-methoxyphenyl)-1,1-dimethylethyl]amino}-ethyl)-2H-1,4-benzoxazin-3-(4H)-one) is known as a selective $\beta_2$ adrenergic receptor agonist, which is represented by the following formula:

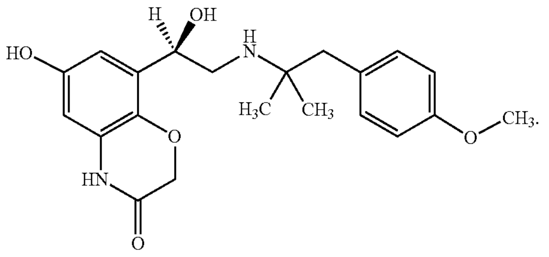 [SMILES: COc1ccc(CC(C)(C)NC[C@H](O)c2cc(O)cc3c2OCC(=O)N3)cc1]

Since $\beta_2$ adrenergic receptors are generally present in the bronchi or blood vessels, olodaterol hydrochloride has been launched as a drug for treating chronic obstructive pulmonary disease (COPD) in the form of a combination drug with tiotropium. Effects of olodaterol on the treatment of eye diseases, particularly on dry eye, have not been known so far.

A $\beta_2$ adrenergic receptor antagonist, timolol, is used for a medicament for treating glaucoma or ocular hypertension, and has ocular hypotensive effects. In particular, it is desirable that a $\beta_2$ adrenergic receptor agonist as a medicament for treating dry eye does not substantially impact on the intraocular pressure; i.e., it does not cause side effects such as the increase or reduction of intraocular pressure.

CITATION LIST

Patent Literature

[Patent Literature 1] WO 01/41806
[Patent Literature 2] WO 2011/068786
[Patent Literature 3] WO 2017/043612
[Patent Literature 4] WO 2019/020634

SUMMARY

A problem to be solved by the present invention is to provide a compound useful for preventing or treating dry eye and a medicament for preventing and/or treating dry eye comprising the same which does not substantially impact on intraocular pressure.

The present inventors have extensively studied to solve the above problem, and then surprisingly have found that olodaterol or a salt thereof stabilizes tear film, enhances lacrimal secretion, and/or increases tear volumes, which may prevent and/or treat dry eye without a substantial impact on intraocular pressure, and have achieved the invention.

In one embodiment, a medicament for preventing and/or treating dry eye, comprising olodaterol or a salt thereof as an active ingredient, is provided. In another embodiment, an agent for stabilizing tear film, comprising olodaterol or a salt thereof as an active ingredient, is provided. In still another embodiment, an agent for enhancing lacrimal secretion and/or increasing tear volumes, comprising olodaterol or a salt thereof as an active ingredient, is provided. In still another embodiment, a method of preventing and/or treating dry eye in a subject in need thereof, comprising administering olodaterol or a salt thereof to the subject is provided.

Olodaterol or a salt thereof may extend the tear film break-up time to stabilize tear film in a dose-dependent manner, and is expected to be useful for prevention and/or treatment of dry eye. Olodaterol or a salt thereof may also enhance tear secretion and increase tear volumes, and May significantly increase tear volumes even in lower concentrations than do other selective $\beta_2$ adrenergic receptor agonists, which allows for the provision of effects on prevention and/or treatment of dry eye with lower exposure. The provision of effects on prevention and/or treatment with low exposure may decrease risks of systemic and/or local side effects. No substantial increase or reduction of intraocular pressure during a prescribed period after administration allows for the provision of a medicament of prevention and/or treatment with high safety to eyes.

BRIEF DESCRIPTION OF DRAWINGS

[FIG. 1]

A figure showing the effect of extending tear film break-up time and time-course changes thereof at each concentration after a single ocular instillation of 0.0001% (w/v), 0.001% (w/v), or 0.01% (w/v) of olodaterol to cynomolgus monkeys.

[FIG. 2]

A figure showing the effect of extending tear film break-up time and time-course changes thereof after a single ocular instillation of 1% (w/v) fenoterol or 1% (w/v) clenbuterol ophthalmic solution to cynomolgus monkeys.

[FIG. 3]

A figure showing the effect of increasing tear volumes and time-course changes thereof at each concentration after a single ocular instillation of 0.00001% (w/v), 0.0001% (w/v), 0.001% (w/v), or 0.01% (w/v) of olodaterol to rats.

[FIG. 4]

A figure showing temporal effects on the intraocular pressure in twice daily repeated administration of 0.01% (w/v) or 0.1% (w/v) of olodaterol ophthalmic solution to cynomolgus monkeys.

DESCRIPTION OF EMBODIMENTS

Several embodiments are illustrated as follows, but are not limited thereto.

[Item 1]

A medicament for preventing and/or treating dry eye, comprising olodaterol or a salt thereof as an active ingredient.

[Item 2]

The medicament according to Item 1, wherein the dry eye accompanies corneal and conjunctival epithelium disorder caused by at least one selected from the group consisting of superficial punctate keratopathy, corneal epithelium defect, corneal erosion, corneal ulcer, conjunctival epithelium defect, keratoconjunctivitis sicca, superior limbic keratoconjunctivitis, filamentary keratoconjunctivitis, non-infectious keratitis, and non-infectious conjunctivitis.

[Item 3]

The medicament according to Item 1, wherein the dry eye is a disease caused by at least one selected from the group consisting of tear film instability, lacrimal hyposecretion, xerophthalmia, tear deficiency, keratoconjunctivitis sicca, lacrimal gland dysfunction, meibomian gland dysfunction, VDT (Visual Display Terminal) operation, use of contact lenses, tear abnormalities, and keratoconjunctivitis.

[Item 4]

The medicament according to any one of Items 1 to 3, wherein the olodaterol or a salt thereof is comprised in a concentration of 0.1% (w/v) or less.

[Item 5]

The medicament according to any one of Items 1 to 3, wherein the olodaterol or a salt thereof is comprised in a concentration of 0.01% (w/v) or less.

[Item 6]

The medicament according to any one of Items 1 to 3, wherein the olodaterol or a salt thereof is comprised in a concentration of 0.00001 to 0.01% (w/v).

[Item 7]

The medicament according to any one of Items 1 to 3, wherein the olodaterol or a salt thereof is comprised in a concentration of 0.00001 to 0.005% (w/v).

[Item 8]

The medicament according to any one of Items 1 to 3, wherein the olodaterol or a salt thereof is comprised in a concentration of 0.00001 to 0.001% (w/v).

[Item 9]

The medicament according to any one of Items 1 to 8, wherein the medicament is in the form of an eye drop.

[Item 10]

The medicament according to any one of Items 1 to 9, wherein the medicament does not substantially increase and/or reduce intraocular pressure.

[Item 11]

The medicament according to any one of Items 1 to 10, wherein the olodaterol or a salt thereof is olodaterol hydrochloride.

[Item 12]

An agent for stabilizing tear film, comprising olodaterol or a salt thereof as an active ingredient.

[Item 13]

An agent for enhancing lacrimal secretion and/or increasing tear volumes, comprising olodaterol or a salt thereof as an active ingredient.

[Item 14]

A method of preventing and/or treating dry eye, comprising administering a therapeutically effective amount of olodaterol or a salt thereof to a subject.

[Item 15]

Olodaterol or a salt thereof for use in preventing and/or treating dry eye.

[Item 16]

Use of olodaterol or a salt thereof in the manufacture of a medicament for preventing and/or treating dry eye.

[Item 17]

A method of preventing and/or treating dry eye in a subject in need thereof, comprising administering a therapeutically effective amount of olodaterol or a salt thereof to the subject, including a human and a mammal except for a human.

[Item 18]

The method according to Item 17, wherein the dry eye accompanies corneal and conjunctival epithelium disorder caused by at least one selected from the group consisting of superficial punctate keratopathy, corneal epithelium defect, corneal erosion, corneal ulcer, conjunctival epithelium defect, keratoconjunctivitis sicca, superior limbic keratoconjunctivitis, filamentary keratoconjunctivitis, non-infectious keratitis, and non-infectious conjunctivitis.

[Item 19]

The method according to Item 17, wherein the dry eye is a disease caused by at least one selected from the group consisting of tear film instability, lacrimal hyposecretion, xerophthalmia, tear deficiency, keratoconjunctivitis sicca, lacrimal gland dysfunction, meibomian gland dysfunction, VDT (Visual Display Terminal) operation, use of contact lenses, tear abnormalities, and keratoconjunctivitis.

[Item 20]

The method according to any one of Items 17 to 19, wherein the olodaterol or a salt thereof is administered in a concentration of 0.1% (w/v) or less.

[Item 21]

The method according to any one of Items 17 to 19, wherein the olodaterol or a salt thereof is administered in a concentration of 0.01% (w/v) or less.

[Item 22]

The method according to any one of Items 17 to 19, wherein the olodaterol or a salt thereof is administered in a concentration of 0.00001 to 0.01% (w/v).

[Item 23]

The method according to any one of Items 17 to 19, wherein the olodaterol or a salt thereof is administered in a concentration of 0.00001 to 0.005% (w/v).

[Item 24]

The method according to any one of Items 17 to 19, wherein the olodaterol or a salt thereof is administered in a concentration of 0.00001 to 0.001% (w/v).

[Item 25]

The method according to any one of Items 17 to 24, wherein the olodaterol or a salt thereof is administered in the form of an eye drop.

[Item 26]

The method according to any one of Items 17 to 25, wherein administering the olodaterol or a salt thereof does not substantially increase and/or reduce intraocular pressure.

[Item 27]

The method according to any one of Items 17 to 26, wherein the olodaterol or a salt thereof is olodaterol hydrochloride.

[Item 28]

A method of stabilizing tear film in a subject in need thereof, comprising administering a therapeutically effective amount of olodaterol or a salt thereof to the subject.

[Item 29] A method of enhancing lacrimal secretion and/or increasing tear volumes in a subject in need thereof, comprising administering a therapeutically effective amount of olodaterol or a salt thereof to the subject.

[Item 30]

A method of preventing and/or treating dry eye in a subject in need thereof, comprising administering a therapeutically effective amount of olodaterol or a salt thereof to the subject,

- wherein the olodaterol or a salt thereof is administered in a concentration of 0.00001 to 0.01% (w/v),
- wherein the olodaterol or a salt thereof stabilizes tear film and/or enhances lacrimal secretion and/or increases tear volumes, and
- wherein administering the olodaterol or a salt thereof does not substantially increase and/or reduce intraocular pressure.

Olodaterol is a selective agonist for human $\beta_2$ adrenergic receptor, represented by a general formula as below, which shows a weak intrinsic activity against $\beta_1$ adrenergic receptors, while showing almost perfect intrinsic activity against $\beta_2$ adrenergic receptors and having high $\beta_2$ adrenergic receptor selectivity.

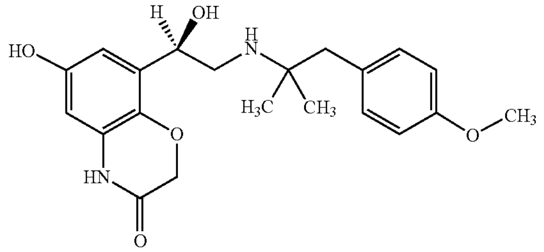

The term "olodaterol or a salt thereof" used herein includes olodaterol and its salt with inorganic or organic acid. Such a salt of olodaterol includes, for example, hydrochloride, hydrosulfate, acetate, trifluoroacetate, hydrobromide, hydroiodide, hydrophosphate, hydromethanesulfonate, hydronitrate, hydromaleate, hydroacetate, hydrobenzoate, hydrocitrate, hydrofumarate, hydrotartrate, hydrooxalate, hydrosuccinate, hydrobenzoate, and hydro-p-toluenesulfonate; preferably, hydrochloride, hydrobromide, hydrosulfate, hydrophosphate, hydrofumarate, and hydromethanesulfonate; more preferably, olodaterol hydrochloride. Salts can be prepared according to conventional methods in the field of organic synthetic chemistry or the methods described in, for example, wo 2004/045618 and US 2007/0027148 A.

Olodaterol or a salt thereof may be present in the form of a hydrate or a solvate. Such a solvate includes, for example, ethanolate. A hydrate and a solvate can be prepared according to conventional methods in the field of organic synthetic chemistry or may be commercially available.

When olodaterol or a salt thereof has crystal polymorphs and crystal polymorph group (i.e., crystal polymorph system), such crystal polymorphs and crystal polymorph group (i.e., crystal polymorph system) may also be encompassed in the scope of the present invention. When crystalline forms vary depending on conditions and states of preparation, crystallization, and storage of crystals, the crystal polymorph group (i.e., crystal polymorph system) includes not only each crystalline form obtained in each of these steps, but also any mixtures of crystalline forms obtained in two or more of these steps.

Herein, the concentration of olodaterol or a salt thereof in a medicament is not limited, but is preferably 0.1% (w/v) or less and/or below, more preferably 0.01% (w/v) or less and/or below, still more preferably 0.005% (w/v) or less and/or below. The upper limit of the concentration includes 0.1% (w/v), 0.05% (w/v), 0.03% (w/v), 0.01% (w/v), 0.005% (w/v), 0.003% (w/v), and 0.001% (w/v). The lower limit of the concentration includes 0.0000001% (w/v), 0.000001% (w/v), 0.000003% (w/v), 0.000005% (w/v), 0.00001% (w/v), 0.00003% (w/v), 0.00005% (w/v), 0.0001% (w/v), 0.0003% (w/v), and 0.0005% (w/v). The range of the concentrations includes 0.0000001 to 0.1% (w/v), 0.0000001 to 0.05% (w/v), 0.0000001 to 0.03% (w/v), 0.0000001 to 0.01% (w/v), 0.0000001 to 0.005% (w/v), 0.0000001 to 0.003% (w/v), 0.0000001 to 0.001% (w/v), 0.000001 to 0.1% (w/v), 0.000001 to 0.05% (w/v), 0.000001 to 0.03% (w/v), 0.000001 to 0.01% (w/v), 0.000001 to 0.005% (w/v), 0.000001 to 0.003% (w/v), 0.000001 to 0.001% (w/v), 0.000003 to 0.1% (w/v), 0.000003 to 0.05% (w/v), 0.000003 to 0.03% (w/v), 0.000003 to 0.01% (w/v), 0.000003 to 0.005% (w/v), 0.000003 to 0.003% (w/v), 0.000003 to 0.001% (w/v), 0.000005 to 0.1% (w/v), 0.000005 to 0.001% (w/v), 0.05% (w/v), 0.000005 to 0.03% (w/v), 0.000005 to 0.01% (w/v), 0.000005 to 0.005% (w/v), 0.000005 to 0.003% (w/v), 0.000005 to 0.001% (w/v), 0.00001 to 0.1% (w/v), 0.00001 to 0.05% (w/v), 0.00001 to 0.03% (w/v), 0.00001 to 0.01% (w/v), 0.00001 to 0.005% (w/v), 0.00001 to 0.003% (w/v), 0.00001 to 0.001% (w/v), 0.00003 to 0.1% (w/v), 0.00003 to 0.05% (w/v), 0.00003 to 0.03% (w/v), 0.00003 to 0.01% (w/v), 0.00003 to 0.005% (w/v), 0.00003 to 0.003% (w/v), 0.00003 to 0.001% (w/v), 0.00005 to 0.1% (w/v), 0.00005 to 0.05% (w/v), 0.00005 to 0.03% (w/v), 0.00005 to 0.01% (w/v), 0.00005 to 0.005% (w/v), 0.00005 to 0.003% (w/v), 0.00005 to 0.001% (w/v), 0.0001 to 0.1% (w/v), 0.0001 to 0.05% (w/v), 0.0001 to 0.03% (w/v), 0.0001 to 0.01% (w/v), 0.0001 to 0.005% (w/v), 0.0001 to 0.003% (w/v), 0.0001 to 0.001% (w/v), 0.0003 to 0.1% (w/v), 0.0003 to 0.05% (w/v), 0.0003 to 0.03% (w/v), 0.0003 to 0.01% (w/v), 0.0003 to 0.005% (w/v), 0.0003 to 0.003% (w/v), 0.0003 to 0.001% (w/v), 0.0005 to 0.1% (w/v), 0.0005 to 0.05% (w/v), 0.0005 to 0.03% (w/v), 0.0005 to 0.01% (w/v), 0.0005 to 0.005% (w/v), 0.0005 to 0.003% (w/v), and 0.0005 to 0.001% (w/v).

$\beta_2$ adrenergic receptor agonists are known to cause systemic side effects such as cardiovascular side effects (e.g., increase of heart rate and arrhythmia) when also acting on $\beta_1$ subtypes, many of which are present in the heart (Patent Literature 1). Olodaterol or a salt thereof does not substantially show systemic and/or local side effects in any of the above concentrations or less than these concentrations, and is expected to provide a medicament with good tolerability.

Olodaterol or a salt thereof may be administered by formulating into a medicament form comprising the same as an active ingredient. Such a form for administration includes, for example, the form of parenteral administration, preferably the form of ocular instillation. A dosage form includes, for example, an eye drop and an eye ointment, preferably an eye drop, more preferably an aqueous eye drop.

Herein, a medicament may be prepared by formulating an active ingredient with pharmaceutically acceptable carriers. Such pharmaceutically acceptable carriers include, for example, buffering agents, tonicity agents, pH adjusters, preserving agents, stabilizing agents, and vehicles. The amount of the carriers contained in a medicament is not limited, and may be any amounts commonly used in the field.

Dosage, also herein referred to as a "therapeutically effective amount", of a medicament herein is not limited as long as it provides a desired therapeutic efficacy and tolerability. For example, it is preferable to instill 1 to 3 drops at a time per one eye for an eye drop, more preferably 1 or 2 drops at a time, still more preferably 1 drop at a time. It is preferable to instill 1 to 6 times daily per one eye, more preferably 1 to 3 times daily, still more preferably 1 or 2 times daily, particularly preferably once daily. It is further preferable to instill 1 drop at a time 1 or 2 times daily per one eye, more preferably 1 drop at a time once daily. One drop herein usually ranges from about 0.01 mL to about 0.1 mL.

The term "dry eye" used herein is a disease causing dry-eye symptoms such as discomfort feelings on eyes and reduction or abnormalities in visual performance, associated with abnormalities in tear volume or quality, which may cause disorders on the surface of eyes such as cornea. Such dry-eye symptoms include, for example, eye fatigue, itchy eyes, eye pain, tearing, discharge, dryness of eyes, and blurred vision. Dry eye may be associated with and/or caused by at least one selected from the group consisting of corneal and conjunctival epithelium disorder caused by at least one selected from the group consisting of superficial punctate keratopathy, corneal epithelium defect, corneal erosion, corneal ulcer, conjunctival epithelium defect, keratoconjunctivitis sicca, superior limbic keratoconjunctivitis, filamentary keratoconjunctivitis, non-infectious keratitis, and non-infectious conjunctivitis, tear film instability, lacrimal hyposecretion, xerophthalmia, tear deficiency, Sjogren syndrome, keratoconjunctivitis sicca, Stevens-Johnson syndrome, Graves' disease, lacrimal gland dysfunction, meibomian gland dysfunction, diabetes, graft-versus-host disease, VDT (Visual Display Terminal) operation, surgery, medicine, trauma, use of contact lenses, tear abnormalities, and keratoconjunctivitis. Preferably, dry eye may be associated with and/or caused by at least one selected from the group consisting of corneal and conjunctival epithelium disorder caused by at least one selected from the group consisting of superficial punctate keratopathy, corneal epithelium defect, corneal erosion, corneal ulcer, conjunctival epithelium defect, keratoconjunctivitis sicca, superior limbic keratoconjunctivitis, filamentary keratoconjunctivitis, non-infectious keratitis, and non-infectious conjunctivitis, tear film instability, lacrimal hyposecretion, xerophthalmia, tear deficiency, keratoconjunctivitis sicca, lacrimal gland dysfunction, meibomian gland dysfunction, VDT (Visual Display Terminal) operation, use of contact lenses, tear abnormalities, and keratoconjunctivitis.

Herein, the effect of stabilizing tear film is mainly associated with abnormalities in tear quality, and is the effect of extending the tear film break-up time (also herein referred to as "TBUT") which is an index of the tear film stability covering the surface of cornea, which can be assessed by measuring TBUT. Specifically, when the time until tear film covering cornea is disrupted after eyes open unblinkingly is measured, then it may be diagnosed for human beings as normal when the time is 10 seconds or over, and diagnosed as dry eye when the time is 5 seconds or less. TBUT is usually measured with a staining solution such as fluorescein, but the measurement is not limited thereto. More specifically, it can be assessed, for example, under the condition of Test 1 below. When dry eye is associated with tear film instability, dry eye may be short tear film break-up time type of dry eye. A medicament herein may extend TBUT, for example, even at 15 minutes, preferably 30 minutes, more preferably 60 minutes, after administration. The extending effect may depend on the dose of an active ingredient. Other selective $\beta_2$ adrenergic receptor agonists did not have the TBUT-extending effect as shown in Test 2 below, whereas olodaterol showed the sustained TBUT-extending effect even in low concentrations as shown in Test 1. The effect of olodaterol on stabilizing tear film is considered to be extraordinary, unlike other $\beta_2$ adrenergic receptor agonists.

Herein, the effect of increasing tear volumes is the effect of improving tear volumes and/or tear quality, which enhances the secretion of tears and/or tear proteins. The effect of increasing tear volumes can be assessed by measuring the amount of lacrimal secretion under, for example, Schirmer's test. Specifically, it can be assessed under, for example, the condition of Test 3 below. When dry eye is associated with a decrease in the amount of lacrimal secretion, dry eye may be aqueous deficient dry eye, and may be associated with Sjogren syndrome. When dry eye is associated with abnormalities in tear quality, dry eye may be evaporative dry eye, and may be associated with meibomian gland dysfunction. The effect of increasing tear volumes may be elicited even by olodaterol in low concentrations, for example, 0.1% (w/v) or less, 0.01% (w/v) or less, 0.001% (w/v) or less, and 0.0001% (w/v) or less. The effect of increasing tear volumes may be sustained for, for example, 0.5 hours or more, 2 hours or more, 8 hours or more, and 16 hours or more, after ocular instillation.

The phrase "does not substantially increase and/or reduce intraocular pressure" used herein means the case where no significant difference in intraocular pressure is produced compared to a control in a single administration or repeated administration of an active ingredient to a subject for a certain period. In one embodiment, the phrase "does not substantially increase and/or reduce intraocular pressure" means the case where no significant difference in intraocular pressure is produced compared to a control in once-daily administration or two- to six-times-daily repeated administration of 0.1% (w/v) or less of an active ingredient to a subject, for example, immediately after administration, or at 2 hours, 4 hours, 2 days, 7 days, or 14 days, after administration, and the intraocular pressure can be assessed under, for example, the condition of Test 5 below.

The term "preventing" used herein includes the prevention and delay of the onset of dry eye symptoms. Olodaterol or a salt thereof may stabilize tear film and increase tear volumes, and is expected to be useful for the prevention of dry eye.

The term "treating" used herein includes the alleviation, improvement, and remission of dry eye symptoms, and the inhibition, prevention, and delay of progression.

Examples

The invention is illustrated in more detail by Examples and Tests below, but is not intended to be limited thereto. Concentrations refer to weight to volume % "w/v (g/100 mL) %", unless otherwise specified.

[Test 1] Effect of Extending Tear Film Break-Up Time

The effect of olodaterol ophthalmic solutions on extension of tear film break-up time was studied.

(Sample Preparation)

The following ophthalmic solution 1 was prepared as an olodaterol ophthalmic solution for use in the test.

Ophthalmic Solution 1:

Olodaterol hydrochloride (0.0001 g), a buffering agent, and a tonicity agent were dissolved in water so as to be 100 mL, and a pH adjuster was added to the solution to prepare an olodaterol ophthalmic solution in the concentration of 0.0001% (w/v).

Olodaterol ophthalmic solutions in the concentrations of 0.001 and 0.01% (w/v) were also prepared with varied amounts of olodaterol hydrochloride.

An ophthalmic solution without containing olodaterol (vehicle) was prepared as a control group for the olodaterol ophthalmic solution groups.

(Method)

TBUT measurement tests were conducted for 10 normal male cynomolgus monkeys by partial crossover design of 5 monkeys per group. The test animals were given general anesthesia by intramuscular injection with ketamine hydrochloride (Ketalar for intramuscular injection 500 mg (registered trademark), Daiichi Sankyo Company, Limited.), and then were let their eyes closed. Then, TBUT was measured before and at 15, 30, and 60 minutes after ocular instillation of a vehicle or each ophthalmic solution (20 μL/eye) to the right eye. Specifically, 1% fluorescein solution (2 μL/eye) was instilled, and the time right after opening of the eyelids until breaking of the fluorescein layer (tear film) on the cornea was measured three times under a slit lamp, followed by calculation of the average. (N=5 eyes)

(Results)

Test results are shown in FIG. 1.

Discussion

As shown in FIG. 1, the TBUT-extending effect was confirmed in a concentration-dependent manner in the ocular instillation of olodaterol. The TBUT-extending effect was not observed in ocular instillation of a vehicle.

Accordingly, olodaterol has the remarkable effect of stabilizing tear film, and is useful for a medicament for preventing and/or treating dry eye. In particular, it was indicated to be useful for a medicament for preventing and/or treating short tear film break-up time type of dry eye.

[Test 2] Effect of Extending Tear Film Break-Up Time

The effects of fenoterol and clenbuterol ophthalmic solutions on extension of tear film break-up time were studied.

(Sample Preparation)

The following ophthalmic solution 2 and ophthalmic solution 3 were prepared as a fenoterol ophthalmic solution and clenbuterol ophthalmic solution, respectively, for use in the test.

Ophthalmic Solution 2: (1%)

Fenoterol hydrobromide (1 mg; was dissolved in physiological saline and water so as to be 100 μL, and a pH adjuster was added to the solution to prepare a fenoterol ophthalmic solution in the concentration of 1% (w/v).

Ophthalmic Solution 3: (1%)

Clenbuterol hydrochloride (1 mg) was dissolved in physiological saline and water so as to be 100 μL, and a pH adjuster was added to the solution to prepare a clenbuterol ophthalmic solution in the concentration of 1% (w/v).

(Method)

TBUT was measured in a similar manner to the method of Test 1. (N=4 or 5 eyes)

(Results)

Test results are shown in FIG. 2.

Discussion

As shown in FIG. 2, the extension of TBUT was not confirmed in the fenoterol ophthalmic solution and clenbuterol ophthalmic solution, and the effect of stabilizing tear film was not observed. Whereas, as shown in FIG. 1, olodaterol, a selective $\beta_2$ adrenergic receptor agonist likewise, was confirmed to show the effect of stabilizing tear film even in a low concentration of 0.0001%. It was indicated that the effect of stabilizing tear film shown in olodaterol was not common to selective $\beta_2$ adrenergic receptor agonists, but was characteristic of olodaterol.

Accordingly, olodaterol has the unique and remarkable effect of stabilizing tear film, and is useful for a medicament for preventing and/or treating dry eye. In particular, it is expected to be useful for a medicament for preventing and/or treating short tear film break-up time type of dry eye.

[Test 3] Effect of Increasing Tear Volumes

The effect of olodaterol ophthalmic solutions on increase of the quantity of tears was studied.

(Sample Preparation)

The following ophthalmic solution 4 was prepared as an olodaterol ophthalmic solution for use in the test.

Ophthalmic Solution 4:

Olodaterol hydrochloride (0.00001 g), a buffering agent, and a tonicity agent were dissolved in water so as to be 100 mL, and a pH adjuster was added to the solution to prepare an olodaterol ophthalmic solution in the concentration of 0.00001% (w/v).

Olodaterol ophthalmic solutions in the concentrations of 0.0001, 0.001, and 0.01% (w/v) were also prepared with varied amounts of olodaterol hydrochloride.

An ophthalmic solution without containing olodaterol (vehicle) was prepared as a control group for the olodaterol ophthalmic solution groups.

(Method)

Preparation of Dry-Eye Model

A somnopentyl injection five-fold diluted with physiological saline was intraperitoneally administered to a normal male SD (Sprague-Dawley) rat by 2.5 mL/kg, and the rat was given general anesthesia, followed by keeping the anesthetized state by inhalation of about 1 to 3% isoflurane. Then, the skin on each cheek was incised to remove the exorbital lacrimal gland, followed by suturation with a Michel suture clamp. In this test, an individual wherein reduction of tears was confirmed after 13 weeks from the removal of exorbital lacrimal gland was included as the experimental animal.

Measurement of Quantity of Tears

The quantity of tears was measured with Schirmer strip before and at a prescribed time after ocular instillation of a vehicle or each ophthalmic solution. Specifically, pentobarbital was intraperitoneally administered right after (0 hour), 1.5 hours, 7.5 hours, and 15.5 hours after ocular instillation of a vehicle or each ophthalmic solution to both eyes (5 μL/eye). Half an hour after treatment of general anesthesia, Schirmer strip (1 mm×17 mm) was inserted to conjunctival sac of the lower eyelid of a rat, and then after 1 minute of the insertion, the wet part of the Schirmer strip was measured in increments of 0.5 mm. (N=14 or 16 eyes)

(Results)

Test results are shown in FIG. 3.

Discussion

As shown in FIG. 3, lacrimal secretion was enhanced in the olodaterol-instilled groups, and in the 0.0001 to 0.01% olodaterol-instilled groups, lacrimal secretion was highly enhanced even at 8 hours after ocular instillation. In the higher-concentration groups, the 0.001 and 0.01% olodaterol-instilled groups, the increase of tear volumes was observed even at 16 hours after ocular instillation, which showed the sustained effect of enhancing lacrimal secretion over a long time. Accordingly, olodaterol is useful for a medicament for preventing and/or treating dry eye, and in particular, it is expected to be useful for a medicament for preventing and/or treating aqueous deficient dry eye.

[Test 4] Effect of Increasing Tear Volumes

The effects of fenoterol and clenbuterol ophthalmic solutions on increase of the quantity of tears was studied.

(Sample Preparation)

The following ophthalmic solution 5 and ophthalmic solution 6 were prepared as a fenoterol ophthalmic solution and clenbuterol ophthalmic solution, respectively, for use in the test.

Ophthalmic Solution 5:

Fenoterol hydrobromide (0.0001 g), a buffering agent, and a tonicity agent were dissolved in water so as to be 100 mL, and a pH adjuster was added to the solution to prepare a fenoterol ophthalmic solution in the concentration of 0.001% (w/v).

Fenoterol ophthalmic solutions in the concentrations of 0.01, 0.1, and 1% (w/v) were also prepared with varied amounts of fenoterol hydrobromide.

Ophthalmic Solution 6:

Clenbuterol hydrochloride (0.0001 g), a buffering agent, and a tonicity agent were dissolved in water so as to be 100 mL, and a pH adjuster was added to the solution to prepare a clenbuterol ophthalmic solution in the concentration of 0.001% (w/v).

Clenbuterol ophthalmic solutions in the concentrations of 0.01, 0.1, and 1% (w/v) were also prepared with varied amounts of clenbuterol hydrochloride.

An ophthalmic solution without containing fenoterol or clenbuterol (vehicle) was prepared as a control group for the fenoterol or clenbuterol ophthalmic solution groups.

(Method)

The quantity of tears was measured in a similar manner to Test 3. (N=10 eyes)

(Results)

The following Tables 1 and 2 show incremental differences (mm/min) in Schirmer's test between the vehicle-instilled group and the ophthalmic-solution-instilled groups at 0.5 and 8 hours, respectively, after ocular instillation according to the results of Test 3 and Test 4. The symbol "-" in Tables 1 and 2 means not-performed.

TABLE 1

| | Incremental difference in Schirmer's test at 0.5 hours after ocular instillation | | | | | |
|---|---|---|---|---|---|---|
| | 0.00001% | 0.0001% | 0.001% | 0.01% | 0.1% | 1% |
| olodaterol | 2.8 | 6.0 | 7.2 | 6.9 | — | — |
| fenoterol | — | — | 1.8 | 4.8 | 6.1 | 3.6 |
| clenbuterol | — | — | 2.0 | 2.7 | 3.6 | 3.0 |

TABLE 2

| | Incremental difference in Schirmer's test at 8 hours after ocular instillation | | | | | |
|---|---|---|---|---|---|---|
| | 0.00001% | 0.0001% | 0.001% | 0.01% | 0.1% | 1% |
| olodaterol | 0.4 | 1.7 | 2.1 | 2.8 | — | — |
| fenoterol | — | — | 0.0 | 0.2 | 0.9 | 1.1 |
| clenbuterol | — | — | 0.3 | 1.1 | 2.4 | 3.9 |

Discussion

According to the results in Table 1, olodaterol enhanced lacrimal secretion in much lower concentrations than fenoterol and clenbuterol. As shown in the results in Table 2, it was indicated that olodaterol has the remarkable and sustained effect even in a low concentration.

Accordingly, olodaterol has the remarkable effect of enhancing lacrimal secretion, and is useful for a medicament for preventing and/or treating dry eye. In particular, it is expected to be useful for a medicament for preventing and/or treating aqueous deficient dry eye.

[Test 5] Intraocular Pressure Test

The effect of an olodaterol ophthalmic solution on intraocular pressure was studied.

(Sample Preparation)

Ophthalmic solutions 1 (0.01 and 0.1%) were prepared as an olodaterol ophthalmic solution in a similar manner to Test 1 for use in the test. An ophthalmic solution without containing olodaterol (vehicle) was prepared as a control group for the olodaterol ophthalmic solution groups.

(Method)

Intraocular-pressure measurement tests were conducted for 9 normal male cynomolgus monkeys by partial crossover design of 3 monkeys per group. A vehicle or each ophthalmic solution (20 μL/eye) was instilled to the right eye of the test animals twice daily repeatedly, and the intraocular pressure was measured right before and at 2 hours after the ocular instillation on Day 1, 7, and 14 and at 4 hours after the ocular instillation on Day 1. Specifically, one drop of 0.4% oxybuprocaine hydrochloride ophthalmic solution (trade name: Benoxil (registered trademark) ophthalmic solution 0.4%) was instilled to the right eye so as to provide surface anesthesia, and then the intraocular pressure was measured three times with Mentor tonometer (applanation), followed by calculation of the average. (N=6 eyes)

(Results)

Test results are shown in FIG. 4.

Discussion

As shown in FIG. 4, 0.01% and 0.1% olodaterol ophthalmic solutions did not show increase and/or decrease the intraocular pressure. Accordingly, olodaterol is expected to be a medicament without causing side effects that impact on the intraocular pressure.

INDUSTRIAL APPLICABILITY

Olodaterol or a salt thereof may stabilize tear film and sustainably increase tear volumes even in a low concentration, and is expected to be useful for the prevention and/or treatment of dry eye.

What is claimed is:

1. A method of stabilizing tear film in a subject in need thereof, comprising administering a therapeutically effective amount of olodaterol hydrochloride to the subject.

2. The method according to claim 1, wherein the olodaterol hydrochloride is administered in a concentration of 0.1% (w/v) or less.

3. The method according to claim 1, wherein the olodaterol hydrochloride is administered in a concentration of 0.01% (w/v) or less.

4. The method according to claim 1, wherein the olodaterol hydrochloride is administered in a concentration of 0.00001 to 0.1% (w/v).

5. The method according to claim 1, wherein the olodaterol hydrochloride is administered in a concentration of 0.00001 to 0.01% (w/v).

6. The method according to claim 1, wherein the olodaterol hydrochloride is administered in a concentration of 0.00001 to 0.005% (w/v).

7. The method according to claim 1, wherein the olodaterol hydrochloride is administered in a concentration of 0.00001 to 0.001% (w/v).

8. The method according to claim 1, wherein the olodaterol hydrochloride is administered in a concentration of 0.0001 to 0.001% (w/v).

9. The method according to claim 1, wherein the olodaterol hydrochloride is administered in the form of an eye drop.

10. The method according to claim 1, wherein administering the olodaterol hydrochloride does not substantially increase and/or reduce intraocular pressure.

* * * * *